(12) United States Patent
Gawande et al.

(10) Patent No.: US 9,980,497 B2
(45) Date of Patent: May 29, 2018

(54) ANTIMICROBIAL-ANTIBIOFILM COMPOSITIONS AND METHODS OF USE THEREOF

(71) Applicant: KANE BIOTECH INC., Winnipeg (CA)

(72) Inventors: Purushottam V. Gawande, Winnipeg (CA); Karen Lovetri, Winnipeg (CA); Nandadeva Yakandawala, Winnipeg (CA); Gordon Froelich, Selkirk (CA); Srinivasa Madhyastha, Winnipeg (CA)

(73) Assignee: KANE BIOTECH, INC., Winnipeg, Manitoba (CA)

( * ) Notice: Subject to any disclaimer, the term of this patent is extended or adjusted under 35 U.S.C. 154(b) by 0 days. days.

(21) Appl. No.: 14/772,956

(22) PCT Filed: Mar. 6, 2014

(86) PCT No.: PCT/CA2014/050180
§ 371 (c)(1),
(2) Date: Sep. 4, 2015

(87) PCT Pub. No.: WO2014/134731
PCT Pub. Date: Sep. 12, 2014

(65) Prior Publication Data
US 2016/0015047 A1    Jan. 21, 2016

Related U.S. Application Data

(63) Continuation-in-part of application No. PCT/CA2013/050324, filed on Apr. 26, 2013.

(60) Provisional application No. 61/834,654, filed on Jun. 13, 2013, provisional application No. 61/773,912, filed on Mar. 7, 2013.

(30) Foreign Application Priority Data

Apr. 26, 2013    (WO) ................ PCT/CA2013/050324

(51) Int. Cl.
| | | |
|---|---|---|
| A61K 31/198 | (2006.01) |
| A23B 4/027 | (2006.01) |
| A23B 4/20 | (2006.01) |
| A61K 31/194 | (2006.01) |
| A61K 33/30 | (2006.01) |
| A61K 45/06 | (2006.01) |
| A23L 3/3463 | (2006.01) |
| A23L 3/3508 | (2006.01) |
| A23L 3/358 | (2006.01) |
| A23B 4/24 | (2006.01) |
| A23B 7/154 | (2006.01) |
| A23B 7/157 | (2006.01) |

(52) U.S. Cl.
CPC ................ *A23B 4/027* (2013.01); *A23B 4/20* (2013.01); *A23B 4/24* (2013.01); *A23B 7/154* (2013.01); *A23B 7/157* (2013.01); *A23L 3/3463* (2013.01); *A23L 3/3508* (2013.01); *A23L 3/358* (2013.01); *A61K 31/194* (2013.01); *A61K 31/198* (2013.01); *A61K 33/30* (2013.01); *A61K 45/06* (2013.01); *A23V 2002/00* (2013.01)

(58) Field of Classification Search
CPC .............. A61K 2300/00; A61K 31/198; A61L 2300/404
See application file for complete search history.

(56) References Cited

U.S. PATENT DOCUMENTS

| | | | |
|---|---|---|---|
| 2005/0238602 A1 | 10/2005 | Modak et al. | |
| 2006/0100124 A1* | 5/2006 | Mostoller | ............... A01N 59/26 510/382 |
| 2007/0020364 A1* | 1/2007 | Burnett | ............... A23B 4/0056 426/326 |
| 2007/0190176 A1* | 8/2007 | Percival | ................ A01N 37/44 424/618 |

(Continued)

FOREIGN PATENT DOCUMENTS

| | | | |
|---|---|---|---|
| ES | WO 0038545 A1 * | 7/2000 | ............... A23B 4/20 |
| GB | WO 2005104878 A1 * | 11/2005 | ............... A23B 4/20 |
| RU | 2 436 561 | 5/2007 | |

(Continued)

OTHER PUBLICATIONS

The Skin Care Centre. Wound Healing. Jul. 8, 2007. <http://www.skincarecentre.ca/skin_problems_we_treat/common_skin_disorders/wound_healing.htm>.*

(Continued)

*Primary Examiner* — Tracy Liu

(74) *Attorney, Agent, or Firm* — Haug Partners LLP; William S. Frommer

(57) ABSTRACT

Compositions comprising chelating agents, metal ion salts, gelling agents or a buffer, antimicrobials, antibiofilm agents and a pH adjuster or a buffer for the prevention and treatment of wound infections and food-borne diseases involving bacterial biofilms are disclosed. The anti-infective properties of a composition include reduction or killing of anaerobic/aerobic/facultative gram-negative and gram-positive wound infection associated bacteria occurring in polymicrobial biofilms. The composition may be in the form of lotion, cream, ointment, dressing, bandage, rinse, soak, gel, spray, or other suitable forms, including certain devices. Additionally, the invention offers an efficient method of delivering the formulated composition containing one or two chelating agents or chelating agents alone or in combination with a metal ion salt using either a nanoparticle or other efficient delivery systems.

22 Claims, 11 Drawing Sheets

(56) References Cited

U.S. PATENT DOCUMENTS

2008/0020059 A1\* 1/2008 Chiou .................. A61K 31/555
 424/617
2013/0288953 A1\* 10/2013 Carreira ................ A21D 2/267
 514/2.8

FOREIGN PATENT DOCUMENTS

WO   WO 2009/155088      12/2009
WO   WO 2012170975 A1 \* 12/2012  ............... A61K 9/51

OTHER PUBLICATIONS

Russian Office Action dated Oct. 3,2017 (in Russian).
Russian Office Action dated Oct. 3, 2017 (in English).
Federal Service for IntellectualProperty Search Report.
N. Oulahal et al., "Removal of meat bloflims from surfaces by ultrasounds combined with Enzymes and/or a chelating agent", vol. 8, Iss. 2, Jun. 2007, pp. 192.196 (Abstract).

\* cited by examiner

ANTIMICROBIAL-ANTIBIOFILM COMPOSITIONS AND METHODS OF USE THEREOF

CROSS-REFERENCE TO RELATED APPLICATIONS

This application is the National Stage entry under 35 U.S.C. § 371 of International Application No. PCT/CA2014/050180, filed Mar. 6, 2014, which claims the benefit of priority of U.S. Provisional Patent Application No. 61/773,912, filed on Mar. 7, 2013 entitled "ANTIMICROBIAL COMPOSITIONS AND METHODS AND USES THEREOF FOR TREATING AND PREVENTING WOUND INFECTIONS"; is a continuation-in-part application of International Patent Application No. PCT/CA2013/050324 filed Apr. 26, 2013 entitled "ANTIMICROBIAL-ANTIBIOFILM COMPOSITIONS AND METHODS OF USE THEREOF"; and claims the benefit of priority of U.S. Provisional Patent Application No. 61/834,654 filed Jun. 13, 2013 entitled "ANTIMICROBIAL-ANTIBIOFILM COMPOSITIONS AND METHODS OF USE THEREOF". The content of the above-identified patent applications is hereby expressly incorporated by reference into the detailed description hereof.

FIELD OF THE INVENTION

This invention may relate to methods of using antimicrobial and antibiofilm compositions for prevention and treatment of wound infections. It further may relate to methods of formulating the compositions comprising chelating agents, zinc salts, antimicrobials and pharmaceutically acceptable excipients for applications in wound care, disinfectants, cosmetics and medical instruments/devices. More particularly, the invention may relate to an efficient method of delivering a pharmaceutically acceptable formulation containing two or more chelating agents and a zinc salt

BACKGROUND OF THE INVENTION

From a microbiological perspective, the primary function of normal, intact human and animal skin is to control microbial populations that live on the skin surface and to prevent underlying tissue from becoming colonized and invaded by potential pathogens. Exposure of subcutaneous tissue (i.e. a wound) provides a moist, warm and nutritious environment that is conducive to microbial colonization and proliferation.

Since wound colonization is mostly polymicrobial, involving numerous microorganisms that are potentially pathogenic, any wound is at some risk of becoming infected. In the event of an infection a wound fails to heal, the patient suffers increased trauma as well as increased treatment costs. General wound management practices become more resource demanding. Over 2% of the U.S. population suffers from such chronic, non-healing wounds and it costs the U.S. health care system $20 billion a year. Wounds are an enormous problem worldwide in humans as well as in animals.

Thus, concern among health care practitioners regarding the risk of wound infection is justifiable not only in terms of increased trauma to the patient but also in view of its burden on financial resources and the increasing requirement for cost-effective management within the health care system. Most wound infections are caused by *Staphylococcus aureus* (20%), *Staphylococcus epidermidis* (14%), *Enterococci* spp. (12%), *Escherichia coli* (8%), *Pseudomonas aeruginosa* (8%), *Enterobacter* spp. (7%), *Proteus* spp. (3%), *Klebsiella pneumoniae* (3%), *Streptococci* (3%) and *Candida albicans* (3%).

Wounds often have multiple barriers to healing. Wound healing and infection is influenced by the relationship between the ability of bacteria to create a stable, prosperous community within a wound environment and the ability of the host to control the bacterial community. Since bacteria are rapidly able to form their own protective microenvironment (biofilm) following their attachment to a surface, the ability of the host to control these organisms is likely to decrease as the biofilm community matures. Within a stable biofilm community, interactions between aerobic and anaerobic bacteria are likely to increase their net pathogenic effect, enhancing their potential to cause infection and delay healing. Over the last few years, some have linked biofilm to chronic wounds. Microscopic evaluation or chronic wounds showed well organized biofilm with extracellular polymeric substance adhered around colony bacteria in at least 60% of the chronic wounds.

In recent years, there have been numerous efforts to use antibiotics and antimicrobials for the treatment of non-healing, clinically infected wounds in humans as well as in animals. These antimicrobial agents are of varying chemical compositions and can include peptides, antiseptics (U.S. Pat. No. 6,700,032), antibiotics, silver ions/compounds (US patent appl. pub. no. 2005/0035327), chitosan (US patent appl. pub. no. 2006/0210613; U.S. Pat. No. 6,998,509), nitrofurazone, bismuth thiols, and xylitol (WO 2005/058381).

There have been various attempts by others to create wound care devices such as dressings or bandages, gels and ointments comprising antimicrobial agents. For example, U.S. Pat. No. 3,930,000 discloses the use of a silver zinc allantoinate cream for killing. From a microbiological perspective, the primary function of normal, intact human and animal skin is to control microbial populations that live on the skin surface and to prevent underlying tissue from becoming colonized and invaded by potential pathogens. Exposure of subcutaneous tissue (i.e. a wound) provides a moist, warm and nutritious environment that is conducive to microbial colonization and proliferation.

Historically, it has been presumed that the properties of bacteria that cause chronic infections were similar to those of bacteria grown suspended in liquid growth media. However, research over the past 20 years has indicated that many chronic infections are the result of the biofilm mode of microbial growth. Bacteria in biofilms can be 100 to 1000 times more resistant to antibiotics/antimicrobials compared to their planktonic counterparts. Recent studies have demonstrated biofilm as a potential reason why chronic wounds do not heal (Singh and Barbul, Wound Rep Reg. 16: 1, 2008). In addition, James et al. (Wound Rep Reg. 16: 37-44, 2008) has recently demonstrated biofilms in over 60% of bacterial infections associated with chronic wounds such as diabetic foot ulcers, venous leg ulcers and pressure ulcers.

The chronic wound infections are typically persistent infections that develop slowly, seem to be rarely resolved by immune defenses, and respond transiently to antimicrobial therapy. Thus, there is an unmet clinical need for developing wound care products with both the antibiofilm and antimicrobial activity for prevention and treatment of acute as well as chronic wounds that involve biofilms. A composition with both the antibiofilm and antimicrobial activity kills biofilm bacteria that are highly resistant to antibiotics/antimicrobials and to body's immune system by inhibiting biofilm formation and/or by disrupting preformed biofilms. Furthermore, there is also a need for a non-antibiotic wound care or disinfectant composition comprising generally recognized as safe (GRAS).

In an abattoir or meat processing plant, there is a problem of contamination of meat and apparatuses (e.g. mincing machine, cutters, slicers, mixers, fillers, or the like) with food poisoning microbials. In a conventional meat processing plant, sodium hypochlorite is used as an anti-microbial during a sterilizing process of meat. Meat such as carcasses is immersed in a solution of sodium hypochlorite for a certain time. However, there is a problem of safety for a human body of reaction products of sodium hypochlorite adhering to meat.

Thus, there is a need for an anti-microbial for sterilization of meat, with a high degree of safety for humans, and long lasting anti-microbial power. Such an anti-microbial will keep meat fresher longer and decrease or prevent degradation of products.

SUMMARY OF THE INVENTION

The instant invention may provide compositions and methods for prevention, decontamination or treatment of acute and chronic wound infections, or disinfection of fruits, vegetables, meat products, meat and food processing facilities One embodiment of the invention may provide a composition comprising (a) one or more chelating agents, and (b) one or two metal ion salts.

In another embodiment, a composition of the invention comprises: (a) a small amount of at least two chelating agents, (b) a small amount of at least one metal ion salt, wherein the amount of each of components (a) and (b) is sufficient to form an effective anti-infective composition against bacterial infections in wounds and for application as disinfectants.

In yet another embodiment, a composition of the invention comprises: (a) a small amount of at least two chelating agents, (b) a small amount of at least one metal ion salt, and (c) pharmaceutically acceptable excipients.

Still another embodiment of the invention may provide an anti-infective composition comprising two chelating agents and one or two metal ion salts that are effective against bacteria and fungi causing wound infections (infections of cuts, bruises, surgical sites, lacerations, abrasions, punctures, incisions, gunshots, burns, pyoderma, atopic dermatitis, eczema, pressure ulcers, venous and artery leg ulcers diabetic foot ulcers, etc.), cystic fibrosis (CF)-associated infections, community or hospital acquired infections or food-borne diseases.

The compositions of the invention may be for use against one or more infection-associated bacteria or yeasts selected from the group consisting of Methicillin-resistant *Staphylococcus aureus* (MRSA), *Staphylococcus epidermidis*, Coagulase negative staphylococci (CoNS), Vancomycin resistant *Enterococci* (VRE), Carbapenem resistant *Klebsiella pneumoniae, Pseudomonas aeruginosa, Acinetobacter baumannii*, Methicillin resistant *Staphylococcus pseudintermedius* (MRSP), *Malassezia pachydermatis, Salmonella typhimurium, Escherichia coli* O157:H7, *Candida albicans, Listeria monocytogenes, Campylobacter jejuni, Bacillus* spp., *Streptococcus agalactiae, Streptococcus uberis, Esherichia coli, Salmonella choleraesuis, Stenotrophomonas maltophilia, Enterococcus faecalis, Proteus mirabilis, Klebsiella* spp., *Enterobacter* spp., and *Citrobacter* spp.

A further embodiment of the invention may provide an anti-infective composition comprising at least two chelating agents and one are two metal ion salts that are for use against veterinary wound infections, or mastitis and otitis associated bacteria and yeasts.

In an embodiment, the chelating agent is between about 5000 mg/L and about 50000/L of the composition. In an embodiment, the metal ion salt is between about 1000 mg/L and about 10000 mg/L of the composition.

The chelating agents may be selected from the group consisting of EDTA, EGTA, DTPA, EDDHA, IDA, CDTA, HEDTA, HEIDA, NTA, sodium citrate, potassium citrate, ovotransferrin and lactoferrin. The metal ion salts may be selected from the group consisting of zinc chloride, zinc lactate, zinc citrate, zinc gluconate, zinc sulfate zinc acetate, silver ion or silver sulfadiazine, silver sulfate, silver nitrate, and silver carbonate.

In another embodiment, the chelating agents are EDTA and sodium citrate, and metal ion salt is zinc chloride or zinc sulfate. The EDTA may be present at about 10 mg/ml and sodium citrate may be present at about 10 mg/ml. The zinc chloride or zinc lactate may be present at about 1 mg/ml.

The composition may further comprise one or more ingredients selected from the group consisting of: water, citrate buffer, citric acid, stabilizing agent, a flavoring agent, vitamins, minerals, herbals, a surfactant, an antimicrobial peptide, an antimicrobial and a pH adjuster.

The invention may also teach methods of preparing a suitable formulation for wound care application in a variety of ways, for example in a disinfecting solution, a lotion, cream, a gel, a spray, a thermoreversible gel spray, a paste, a balm, a bandage, a dressing, a gauze, a wound irrigating device, a wrap, and mastitis teat dip solutions.

The invention further may teach methods of preparing suitable formulations for disinfectants and cosmetics. The disinfectants have applications in disinfecting fruits, vegetables, food and meat processing facilities, hospitals, barns, medical instruments, and other industrial and institutional facilities. The cosmetics include shampoos and antimicrobial body lotions and creams.

The invention further may teach methods of preventing or treating meat spoilage comprising topical use of the composition on meat or meat or meat products. The method may include one or more of coating, spraying, misting, injecting, soaking, flushing, dipping and rinsing.

The formulations can also include natural or synthetic flavorings and coloring agents. Thickening agents can also be added to compositions of the invention such as guar gum, carbopol, polyethylene glycol, pluronic F-127, sodium alginate, carboxymethyl cellulose, xanthan gum and other pharmaceutically acceptable thickening agents.

Other formulations will be readily apparent to one skilled in the art. A composition of the invention can include antibiofilm enzymes (cellulase, beta-N-acetylgluconase, DispersinB, papain, DNase 1, etc.), antimicrobial peptides, antibiotics (gentamicin, ciprofloxacin, ampicillin, cefamendole nafate, rifambicin, etc.), antimicrobials (triclosan, chlorhexidine, quaternary ammonium compounds, silver, silver salts, etc.) and other antibiofilm compounds.

The invention may also teach the use of liposomal or nanoparticle delivery systems that enhance the stability and efficacy of anti-infective compounds in the compositions.

DETAILED DESCRIPTION OF THE INVENTION

Definitions

Figure 1:
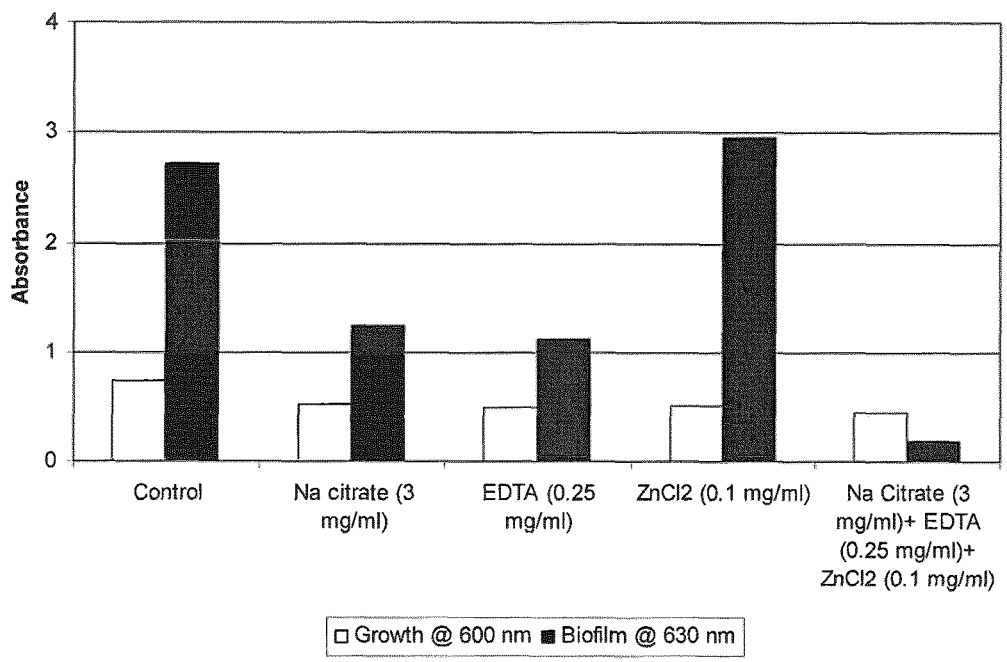
FIG. 1 is a bar graph showing the inhibitory effect of sodium citrate (3 mg/ml), EDTA (0.25 mg/ml) and $ZnCl_2$ (0.1 mg/ml) alone and in combination on methicillin-resistant *Staphylococcus aureus* (MRSA) growth and biofilm formation

The term "antimicrobial" refers to a compound or a composition that kills or inhibits or stops the growth of microorganisms, including, but not limited to bacteria and yeasts.

The term "biofilm" refers to a structured community of microorganisms enclosed in a self produced extracellular polymeric matrix, and attached to a biotic or abiotic surface. Bacteria in a biofilm can be 1000 times more resistant to antibiotics/antimicrobials compared to their planktonic (free living) counterparts.

The term "biofilm formation" refers to the attachment of microorganisms to surfaces and the subsequent development of multiple layers of cells.

The term "antibiofilm' refers to inhibition of microbial biofilm formation and disruption or dispersal of preformed biofilms.

The term "infection" refers to the invasion and multiplication of microorganisms such as bacteria, viruses, and parasites that are not normally present within the body. An infection may cause no symptoms and be subclinical, or it may cause symptoms and be clinically apparent. An infection may remain localized, or it may spread through the blood or lymphatic vessels to become systemic (body wide). Microorganisms that live naturally in the body are not considered infections.

The term "wound" refers to a type of injury in which skin is torn, cut, or punctured (an open wound), or where blunt force trauma causes a contusion (a closed wound). In pathology, it specifically refers to a sharp injury, damages to the dermis of the skin.

The term "acute wound" refers to those that are new and in the first phase of healing. Acute wounds are characterized by skin layers that have been punctured or broken through by an external force or object. Any acute wound can progress to a chronic wound if it does not heal within the expected time frame or as a result of poor blood supply, oxygen, nutrients or hygiene. Acute wounds should be properly treated to avoid infection, inflammation or constant pressure. Acute wounds are categorized based on causes such as lacerations, abrasions, punctures, incisions, gunshots, burns, and type according to the size and depth (superficial or deep).

The term "chronic wound" refers to a wound that just will not repair itself over time. Chronic wounds are often thought to be "stuck" in one of the phases of wound healing, and are most often seen in the older adult population. Typically, if a wound is not healing as expected within 2-3 months, it is considered chronic. Chronic wounds include pressure ulcers (e.g. bed sores), arterial and venous leg ulcers, and diabetic ulcers.

The term "disinfectants" refers to substances that are applied to non-living objects to destroy microorganisms that are living on the objects. Disinfection does not necessarily kill all microorganisms, especially resistant bacterial spores; it is less effective than sterilization, which is an extreme physical and/or chemical process that kills all types of life. Disinfectants are different from other antimicrobial agents such as antibiotics, which destroy microorganisms within the body, and antiseptics, which destroy microorganisms on living tissue. Disinfectants are also different from biocides—the latter are intended to destroy all forms of life, not just microorganisms. Disinfectants work by destroying the cell wall/membrane of microbes or interfering with metabolism and growth.

The term "inhibition" refers to at least a decrease of wound-associated bacterial growth and biofilm formation.

The term "mammal" for purposes of treatment refers to any animal classified as a mammal, including humans, domestic and farm animals, and zoo, sports or pet animals, such as dogs, horses, cats, cattle, pigs, sheep, etc.

The term "prevention" refers to at least preventing a condition associated with bacteria occurring in a mammal, particularly when the mammal is found to be predisposed to having the condition but has not yet been diagnosed as having it.

The term "subject" refers to a living vertebrate such as mammal (preferably human and pet animals) in need of treatment.

The term "therapeutically effective amount" refers to a quantity of a composition high enough to provide a significant positive modification of the subject's condition(s) to be treated.

A "preventative amount" as used herein includes a prophylactic amount, for example, an amount effective for preventing or protecting against wounds, skin infections and related diseases, and symptoms thereof, and amounts effective for alleviating or healing wounds, skin infections, related diseases, and symptoms thereof. By administering a peptide suitable for use in methods of the invention concurrently with an antimicrobial, the peptide and/or the antimicrobial may be administered in a dosage amount that is less than the dosage amount required when the antimicrobial is administered as a sole active ingredient. By administering lower dosage amounts of active ingredient, side effects associated therewith could be reduced.

The term "treatment" refers to an intervention performed with the intention of preventing the further development or altering the pathology of an existing disorder. Accordingly, "treatment" refers to both therapeutic treatment and prophylactic or preventative measures. Those in need of treatment include those already with the infection as well as those in which the infection is to be prevented. In regards to wound infections, "treating or treatment" is intended to mean at least the mitigation of wound healing conditions associated with bacterial infections in a subject, such as a mammal, including but not limited to, a human, that is affected at least in part by the condition, and includes, but is not limited to, modulating, inhibiting the condition, and/or alleviating the condition.

The term "metal ion salt" refers to salt of a metal ion such as zinc chloride, zinc lactate, zinc citrate, zinc gluconate, zinc sulfate zinc acetate, silver ion or silver sulfadiazine, silver sulfate, silver nitrate, and silver carbonate.

The present invention may teach anti-infective compositions offering antimicrobials and antibiofilm activity, containing combinations of chelating agents with other antimicrobial agents, such as, for example, antimicrobials/antibiofilm compounds, metal ion salts with gelling agents, surfactants or stabilizing agents.

Novel compositions that combine chelating agents together with metal ion salts such that lesser quantities of chelating agents and/or metal ion salts than would normally be necessary for an antimicrobial composition are used to achieve significant bacterial growth and biofilm inhibition. Higher concentrations of these compounds can be used if it is desired for certain applications.

The amount of chelating agents to be used in the antimicrobial composition of this invention can be between 10000 to 100000 mg/L. The higher end of this stated range might be used to prepare a concentrated product that would be diluted prior to use. For non-concentrated products, the amount of to be used in this invention is preferably between about 5000 to 10000 mg/L. Preferably, the range is between about 1000 to 5000 mg/L.

The amount of chelating agents to be used should be between about 1000 to 5000 mg/L. The higher end of this range might apply if the compositions were formulated as a concentrate. For non-concentrated products, the amount of chelating agent to be used in this invention is preferably between about 500 to 5000 mg/L. Preferably, the range is between about 1000 to 3000 mg/L, more preferably between about 2000 to 3000 mg/L.

Preparation

By one method, if a two-component composition is formed containing one or two chelating agents and a metal ion salt, these compounds can be combined in the following manner. With good stirring, a chelating agent can be dissolved in water, followed by a metal ion salt. It should be noted, however, that the addition order can be reversed.

Additionally, antimicrobials/antimicrobial peptides, antibiotics, antibiofilm compounds, quaternary ammonium compounds and surfactants also may be advantageously combined with chelating agents in an antimicrobial composition. A composition of the invention comprises: (a) a small amount of at least one or two chelating agent; (b) a small amount of a metal ion salt or iron-sequestering glycoprotein or antimicrobial peptide or an antibiotic or an antibiofilm compound; and (c) a sparing amount of at least one compound from the group consisting of a stabilizing agent and/or a gelling agent and/or a surfactant, wherein, the amount of each of component (a), (b) and (c) is sufficient to form, in combination, an effective anti-infective composition for prevention and treatment of acute and chronic wound infections (infections of cuts, bruises, surgical sites, lacerations, abrasions, punctures, incisions, gunshots, burns, pyoderma, atopic dermatitis, eczema, pressure ulcers, venous and artery leg ulcers diabetic foot ulcers, etc.).

The concentration of active components in the compositions may vary as desired or necessary to decrease the amount of time the composition of the invention is used to prevent or treat wound infections and for disinfection. These variations in active components concentration are easily determined by persons skilled in the art.

Compositions

The present invention may include unique and enhanced anti-infective compositions for the prevention and treatment of wound infections comprising at least two chelating agents and one metal ion salt.

In an embodiment, two chelating agents and a metal ion salt containing composition includes an antimicrobial compound. The chelating agents and a metal ion salt containing composition with an antimicrobial and/antibiofilm compound has an enhanced inhibitory effect on wound infection-associated bacterial growth and biofilm formation. Furthermore, addition of an antimicrobial compound to a composition containing chelating agents and a metal ion salt can make the composition effective against pathogens associated with wound infections and microbial contamination causing food-borne diseases.

In an embodiment of the invention, an enhanced antimicrobial-antibiofilm composition comprises at least one or two chelating agents, one metal ion salt and one or more antimicrobial agents comprising antiseptics (e.g., triclosan, chlorhexidine salt, cetylpyridinium chloride, etc.), antibiotics and bacteriocins (e.g., nisin, epidermin, gallidennin, cinnamycin, duramycin, lacticin 481, etc.), and iron-sequestering glycoproteins (ovotransferrin, lactoferrin and serrotransferrin). Additionally, the wound care or disinfectant compositions may comprise ingredients such as citrate (e.g., citric acid, zinc citrate, sodium citrate, potassium citrate, etc.), minerals (e.g., mineral salts such as zinc chloride, zinc gluconate, zinc lactate, zinc citrate, zinc sulfate, zinc acetate, silver, silver sulfate, silver sulfadiazine, silver nitrate, silver carbonate, etc.), and triterpenoids (e.g., oleanolic acid and ursolic acid) and chitosan In an embodiment, a composition comprises an antibiotic and one or two chelating agents and also one metal ion salt. Antibiotics are well known. Groups of antibiotics include, but are not limited to, β-lactam inhibitors (e.g., penicillin, ampicillin, amoxicillin, methicillin, etc.), cephalosporins (e.g., cephalothin, cephamycin, etc.), aminoglycosides (e.g., streptomycin, tobramycin, etc.), polyenes (e.g., amphotericin, nystatin, etc.), macrolides (e.g., erythromycin, etc.), tetracyclines (e.g., tetracycline, doxycycline, etc.), nitroimidazole (e.g., metronidazole), quinolones (e.g., nalidixic acid), rifamycins (e.g., rifampin), and sulfonamides (e.g., sulfanilamide), nitroaromatics (e.g., chloramphenicol) and pyridines (e.g., isoniazid).

In an embodiment, a composition comprises an antiseptic, one or two chelating agents and one metal ion salt. Antiseptics are agents that kill or inhibit the growth of microorganisms on the external surfaces of the body. Antiseptics include, but are not limited to, triclosan, chlorhexidine salt, and cetylpyridinium chloride.

In an embodiment, a composition comprises an antibiofilm compound, one or two chelating agents and a metal ion salt. Antibiofilm compounds include, but not limited to, DisperinB, DNase I, Proteinase K, apyrase, cis-2-decenoic acid, alginate lyase, lactoferrin, gallium, cellulase, and 5-fluorouracil.

In an embodiment, a composition is effective for inhibiting growth and biofilm formation in wound infection and food-borne disease associated bacteria. The composition is also effective in disrupting or dispersing preformed biofilms, which makes biofilm-embedded bacteria more susceptible to antimicrobial killing. Under appropriate environmental conditions, such as moisture and pH, infections can be modulated using embodiments of the invention.

An embodiment of the invention may also include other pharmaceutically acceptable vehicles, diluents, and additives such as antioxidants, anti-inflammatory compounds, vitamins, tissue degrading enzymes, buffers and solutes that render the formulation isotonic in the intended recipient; and aqueous and non-aqueous sterile suspensions which may include suspending agents, surfactants and thickening agents.

Wound Care Formulations

A composition of the invention may be added to a variety of formulations suitable for applying/delivering the composition to wounds, including, but not limited to, disinfecting solutions, lotions, creams, gels, sprays, gel spray, bandage, dressings, wraps, gauze, tapes, adhesives and wound irrigation devices. To provide such formulations, a composition of this invention is combined with one or more pharmaceutically acceptable excipients.

Formulations including, but not limited to, pharmaceutically acceptable compositions comprising one or two chelating agents and a metal ion salt in combination with an antiseptic, an antibiotic, an antimicrobial, an iron-sequestering glycoprotein, a bacteriocin, extracellular matrix or chitosan can be prepared by any known method.

In general, methods of manufacturing anti-infective compositions may comprise combining a pharmaceutically acceptable carrier and an effective amount of both chelating agents and a metal ion salt with an antiseptic, an antibiotic, a bacteriocin, an antimicrobial peptide or chitosan.

A variety of carriers and excipients can be used to formulate an embodiment of this invention and are well known. Such pharmaceutically acceptable vehicles include, but are not limited to, water, ethanol, humectants such as polypropylene glycol, glycerol and sorbitol, gelling agents such as cellulose derivatives, polyoxypropylene/polyoxyethylene block copolymers, carboxy methyl cellulose, pluronic F-127, sodium alginate, polyethylene glycol, thickening agents such as Carbopol™ 934.

Method of Treatment

Another aspect of this invention may include a method for treating wound infections, and also for decontaminating wound surfaces as well as food/meat processing facilities. In general, wound infections may be treated by applying to the infected wound of a subject with an effective amount of one or more chelating agents and a metal ion salt in combination with one or more antimicrobial agents effective to reduce wound infections.

Before selling meat such as chicken, beef and pork for consumption, it is necessary to stop or retard the growth of pathogenic microorganisms and it is preferable to kill pathogenic microorganisms such as bacteria which may cause food poisoning due to their presence in the meat. Thus the invention provides method of preventing or treating meat spoilage comprising topical use of the composition of the invention on meat or meat products. The meat or meat products may be one or more of beef, pork, lamb, goat, horse, chicken and fish. The meat or meat products may include intestine or intestinal parts of pigs, cattle, sheep, goats and horses used for making sausage casings. They may further include collagen or cellulose used for making artificial sausage casings The compositions may be applied by one or more of coating, spraying, misting, injecting, soaking, flushing, dipping and rinsing. The flushing may include flushing water lines or meat processing lines and cleaning equipment in meat processing and packaging plants.

For use in treating or disinfecting meat, preferred concentration range of ingredients may include:
  (i) Sodium Citrate: (a) 50,000 mg/L-100,000 mg/L, (b) 25,000 mg/L-50,000 mg/L, (c) 10,000 mg/L-25,000 mg/L, (d) 5,000 mg/L-10,000 mg/L, & (e) 1,000 mg/L-5, 000 mg/L.
  (ii) Disodium EDTA: (a) 10,000 mg/L-25,000 mg/L, (b) 5,000 mg/L-10,000 mg/L, (c) 1,000 mg/L-5,000 mg/L, (d) 500 mg/L-1,000 mg/L, & (e) 100 mg/L-500 mg/L
  (iii) Zinc Chloride: (a) 1,000 mg/L-5,000 mg/L, (b) 500 mg/L-1,000 mg/L, (c) 100 mg/L-500 mg/L, and (d) 10 mg/L-100 mg/L.

In one embodiment, one or more chelating agents and a metal ion salt together is formulated as pharmaceutically acceptable medicament as described herein comprising a carrier and an effective amount of composition comprising one or more chelating agents and a metal ion salt as active ingredients.

An exemplary dosing regime of a wound care composition of this invention is application of a composition to the wound surface of a subject (animal or human) at least once or twice. According to this embodiment, a subject would apply a composition of the invention to the wound surface from one to three times daily depending on the type of wound and severity of infection. For animals or pets, the composition of the invention can be used as a lotion or a cream, or a gel or a spray or a dressing twice or thrice a day.

In a further embodiment of the invention, an enhanced wound anti-infective composition does not present any antibiotic resistance concerns and bio-compatibility/safety issues. Also, the composition of this invention comprising one or two chelating agents (EDTA and sodium citrate) and a metal ion salt (zinc chloride or zinc sulfate or zinc lactate) has GRAS (Generally Recognized as Safe) status and all these ingredients are food as well as feed additives.

The present invention may be better understood with reference to the following examples. These examples are intended to be representative of specific embodiments of the invention, and are not intended as limiting the scope of the invention.

EXAMPLES

Example 1: Inhibitory Effect of Sodium Citrate, EDTA and Zinc Chloride Alone and in Combination on Methicillin-Resistant *Staphylococcus aureus* (MRSA) Growth and Biofilm Formation An overnight broth culture of *S. aureus* was grown in TSB and used as inoculum. 96-well microplates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of plaktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition, comprising sodium citrate, EDTA and zinc chloride showed an enhanced inhibitory effect on biofilm formation, as compared to sodium citrate, or EDTA, or zinc chloride alone (FIG. 1).

Figure 2:
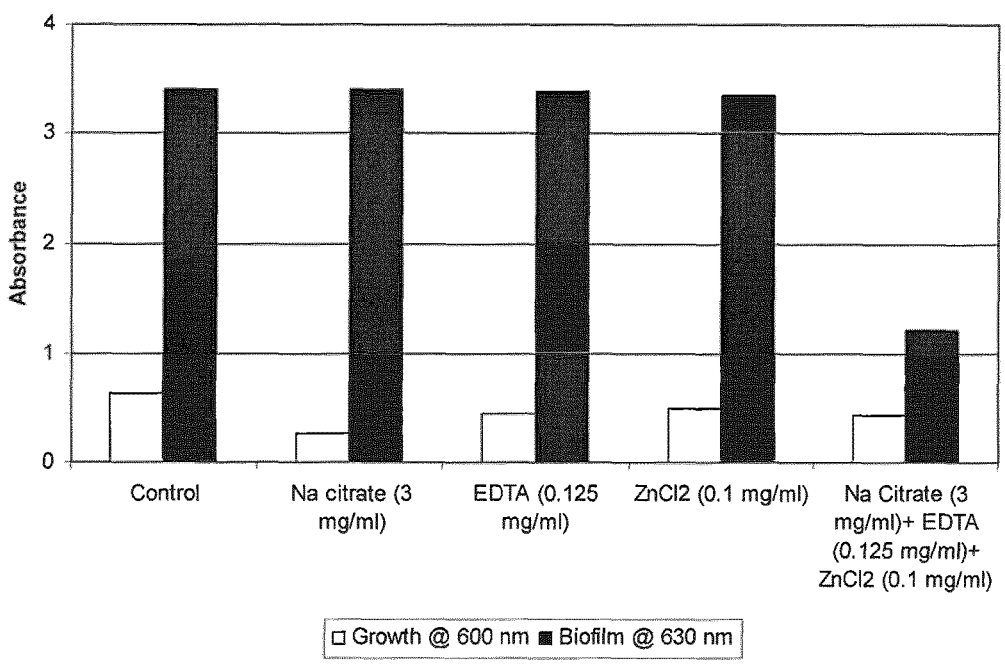
FIG. 2 is a bar graph showing the inhibitory effect of sodium citrate (3 mg/ml), EDTA (0.125 mg/ml) and $ZnCl_2$ (0.1 mg/ml) alone and in combination on methicillin-resistant *Staphylococcus pseudintermedius* (MRSP) growth and biofilm formation

Example 2: Inhibitory Effect of Sodium Citrate, EDTA and Zinc Chloride Alone, and in Combination on Methicillin-Resistant *Staphylococcus pseudintermedius* (MRSP) Growth and Biofilm Formation An overnight broth culture of methicillin resistant *S. pseudintermedius* was grown in TSB and used as inoculum. 96-well microplates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of plaktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition, comprising sodium citrate, EDTA and zinc chloride showed an enhanced inhibitory effect on biofilm formation, as compared to sodium citrate, or EDTA, or zinc chloride alone (FIG. 2).

Figure 3:
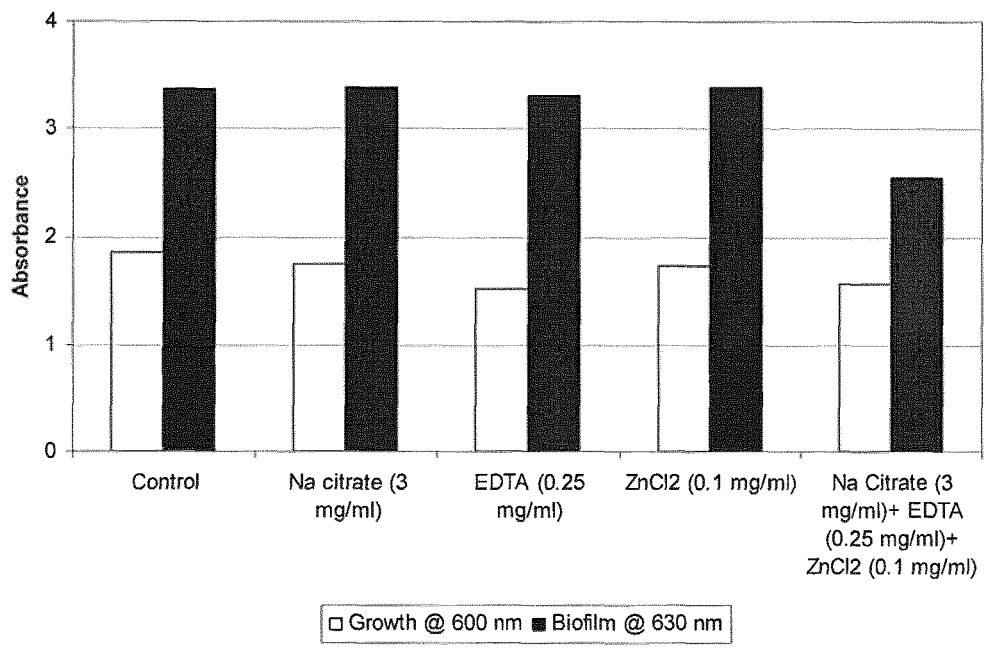
FIG. 3 is a bar graph showing the inhibitory effect of sodium citrate (3 mg/ml), EDTA (0.25 mg/ml) and $ZnCl_2$ (0.1 mg/ml) alone and in combination on *Pseudomonas aeruginosa* growth and biofilm formation

Example 3: Inhibitory Effect of Sodium Citrate, EDTA, and Zinc Chloride Alone, and in Combination on *Pseudomonas aeruginosa* Growth and Biofilm Formation An overnight broth culture of *P. aeruginosa* was grown in TSB and used as inoculum. 96-well microplates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of plaktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition, comprising sodium citrate, EDTA and zinc chloride showed an enhanced inhibitory effect on biofilm formation, as compared to sodium citrate, or EDTA, or zinc chloride alone (FIG. 3).

Figure 4:
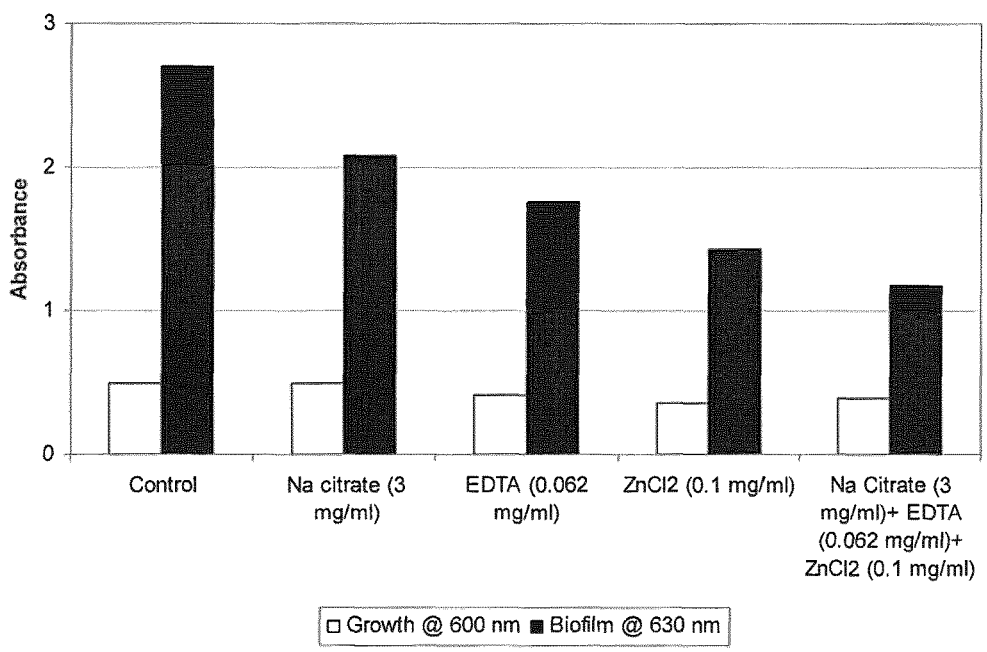
FIG. 4 is a bar graph showing the inhibitory effect of sodium citrate (3 mg/ml), EDTA (0.062 mg/ml) and $ZnCl_2$ (0.1 mg/ml) alone and in combination on *Listeria monocytogenes* growth and biofilm formation

Example 4: Inhibitory Effect of Sodium Citrate, EDTA, and Zinc Chloride Alone and in Combination on *Listeria monocytogenes* Growth and Biofilm Formation An overnight broth culture of *L. monocytogenes* was grown in TSB and used as inoculum. 96-well microplates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of plaktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition, comprising sodium citrate, EDTA and zinc chloride showed an enhanced inhibitory effect on biofilm formation, as compared to sodium citrate, or EDTA, or zinc chloride alone (FIG. 4).

Figure 5:
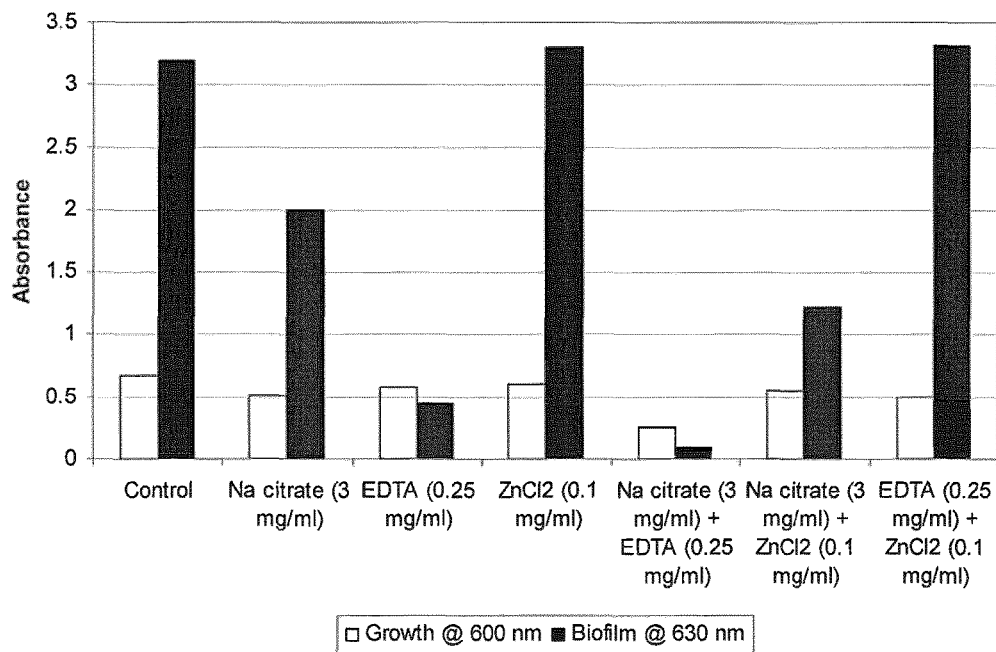
FIG. 5 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$ and EDTA+$ZnCl_2$ combinations on methicillin-resistant *Staphylococcus aureus* (MRSA) growth and biofilm formation

Example 5: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on Methicillin-Resistant *Staphylococcus aureus* [MRSA] Growth and Biofilm Formation An overnight broth culture of *S. aureus* (MRSA) was grown in TSB and used as inoculum. 96-well microplates containing TSB in the absence and the presence of each compound (sodium citrate or EDTA or Zinc chloride) separately and Sodium citrate+EDTA, Sodium citrate+$ZnCl_2$, and EDTA+$ZnCl_2$ combinations were inoculated and incubated at 37° C. for 24 hours. Growth of plaktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA and Sodium citrate+$ZnCl_2$ combinations showed an enhanced inhibitory effect on biofilm formation, as compared to sodium citrate, or EDTA, or zinc chloride alone (FIG. 5).

Figure 6:
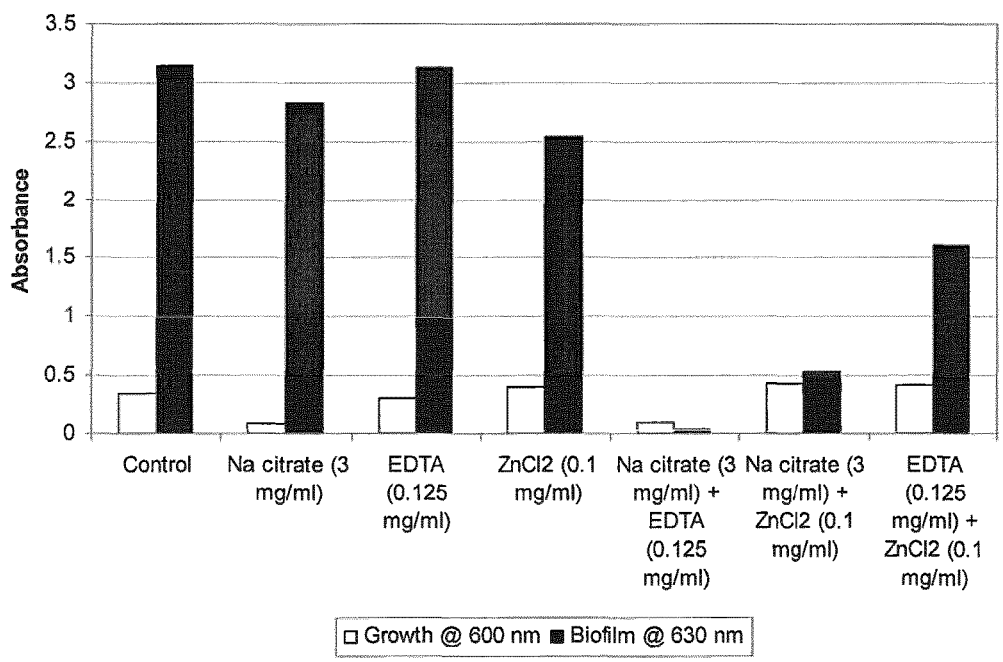
FIG. 6 is a bar graph showing the inhibitory effect of sodium citrate (3 mg/ml), EDTA (0.125 mg/ml) and $ZnCl_2$ (0.1 mg/ml) alone, and sodium citrate+EDTA, sodium citrate+$ZnCl_2$, and EDTA+$ZnCl_2$ combinations on methicillin-resistant *Staphylococcus pseudintermedius* (MRSP) growth and biofilm formation

Example 6: Effect of Sodium Citrate, EDTA, and $ZnCl_2$ Alone, and Sodium Citrate+EDTA, Sodium Citrate+$ZnCl_2$, and EDTA+$ZnCl_2$ Combinations on Methicillin Resistant *Staphylococcus pseudintermedius* (MRSP) Growth and Biofilm Formation An overnight broth culture of MRSP was grown in TSB and used as inoculum. 96-well microplates containing TSB in the absence and the presence of each compound (sodium citrate or EDTA or Zinc chloride) separately and Sodium citrate+EDTA, Sodium citrate+$ZnCl_2$, and EDTA+$ZnCl_2$ combinations were inoculated and incubated at 37° C. for 24 hours. Growth of plaktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA, Sodium citrate+$ZnCl_2$, and EDTA+$ZnCl_2$ combinations showed an enhanced inhibitory effect on biofilm formation, as compared to sodium citrate, or EDTA, or zinc chloride alone (FIG. 6).

Figure 7:
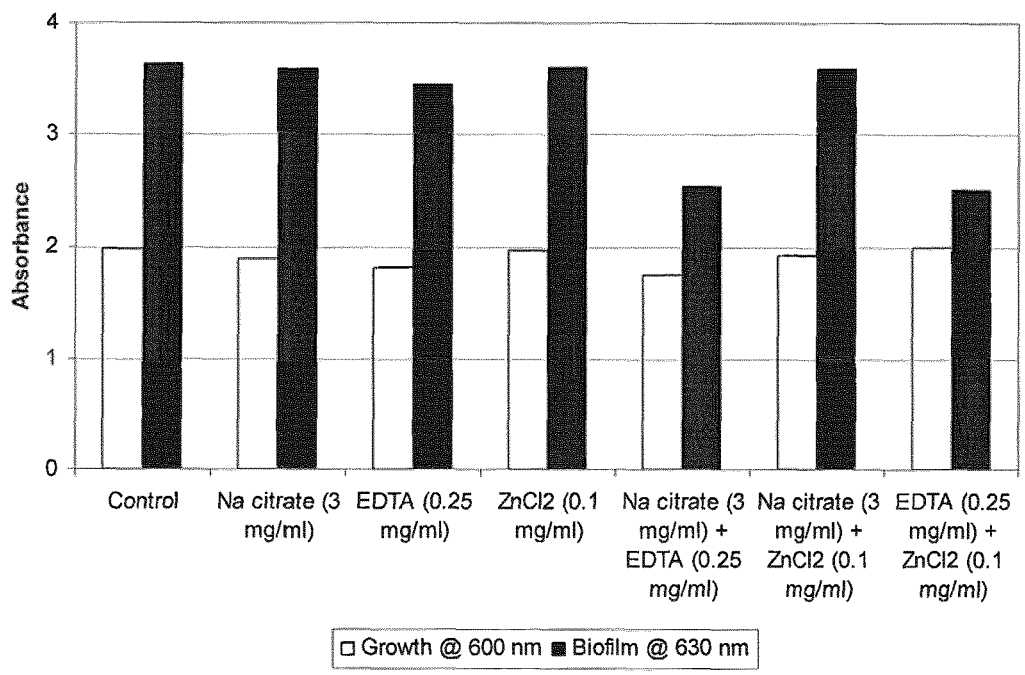
FIG. 7 is a bar graph showing the inhibitory effect of sodium citrate (3 mg/ml), EDTA (0.25 mg/ml), and $ZnCl_2$ (0.1 mg/ml) alone, and sodium citrate+EDTA, sodium citrate+$ZnCl_2$, and EDTA+$ZnCl_2$ combinations on *Pseudomonas aeruginosa* growth and biofilm formation

Example 7: Inhibitory Effect of Sodium Citrate, EDTA, and $ZnCl_2$ Alone, and Sodium Citrate+EDTA, Sodium Citrate+$ZnCl_2$, and EDTA+$ZnCl_2$ Combinations on *Pseudomonas aeruginosa* Growth and Biofilm Formation An overnight broth culture of *P. aeruginosa* was grown in TSB and used as inoculum. 96-well microplates containing TSB in the absence and the presence of each compound (sodium citrate or EDTA or Zinc chloride) separately and Sodium citrate+EDTA, Sodium citrate+$ZnCl_2$, and EDTA+$ZnCl_2$ combinations were inoculated and incubated at 37° C. for 24 hours. Growth of plaktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA, and EDTA+$ZnCl_2$ combinations showed an enhanced inhibitory effect on biofilm formation, as compared to sodium citrate, or EDTA, or zinc chloride alone (FIG. 7).

Example 8: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Salmonella choleraesuis* ATCC 10708

Figure 8:
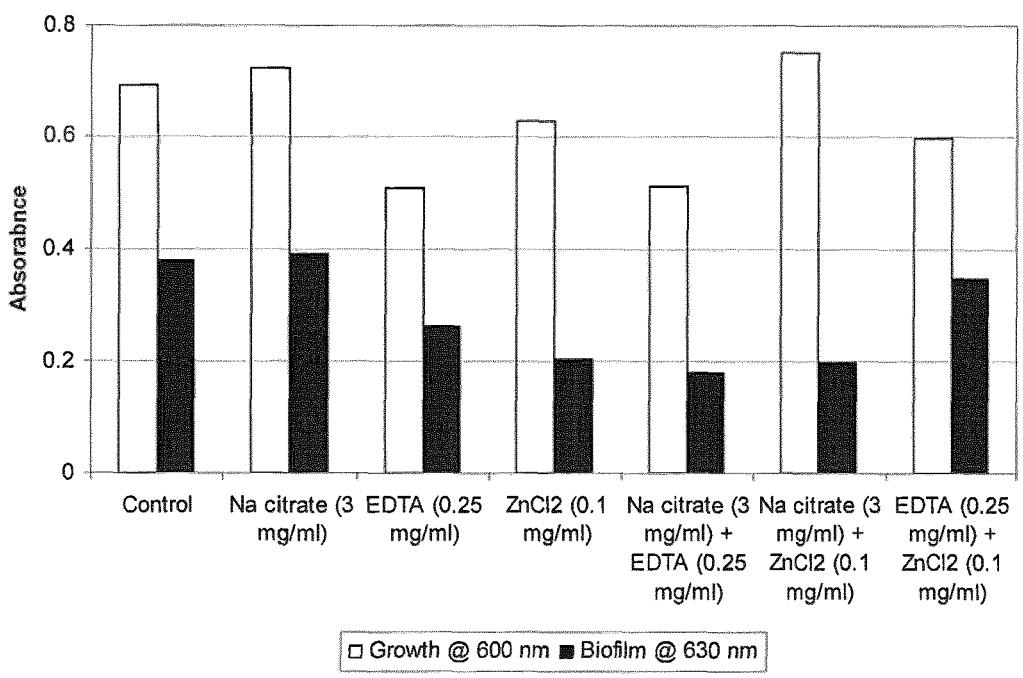
FIG. 8 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Salmonella choleraesuis* ATCC 10708 growth and biofilm formation

An overnight broth culture of *S. choleraesuis* ATCC 10708 was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 8).

Example 9: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Escherichia coli* O157:H7

Figure 9:
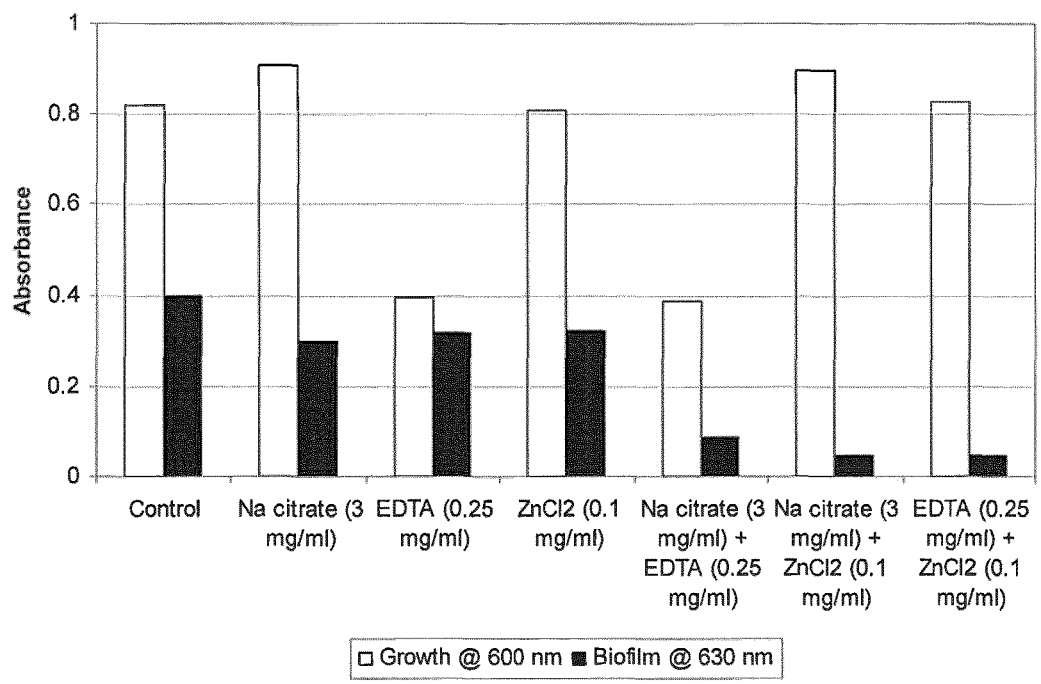
FIG. 9 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Escherichia coli* O157:H7 growth and biofilm formation

An overnight broth culture of *E. coli* O157:H7 was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA, Sodium citrate+ZnCl2, and EDTA+ZnCl2 combinations showed an enhanced inhibitory effect on biofilm formation, as compared to sodium citrate, or EDTA or zinc chloride alone (FIG. 9).

Example 10: Inhibitory Effect of Sodium Citrate, EDTA and $ZnCl_2$ Alone, and in Combination on *Escherichia coli* O157:H7

Figure 10:
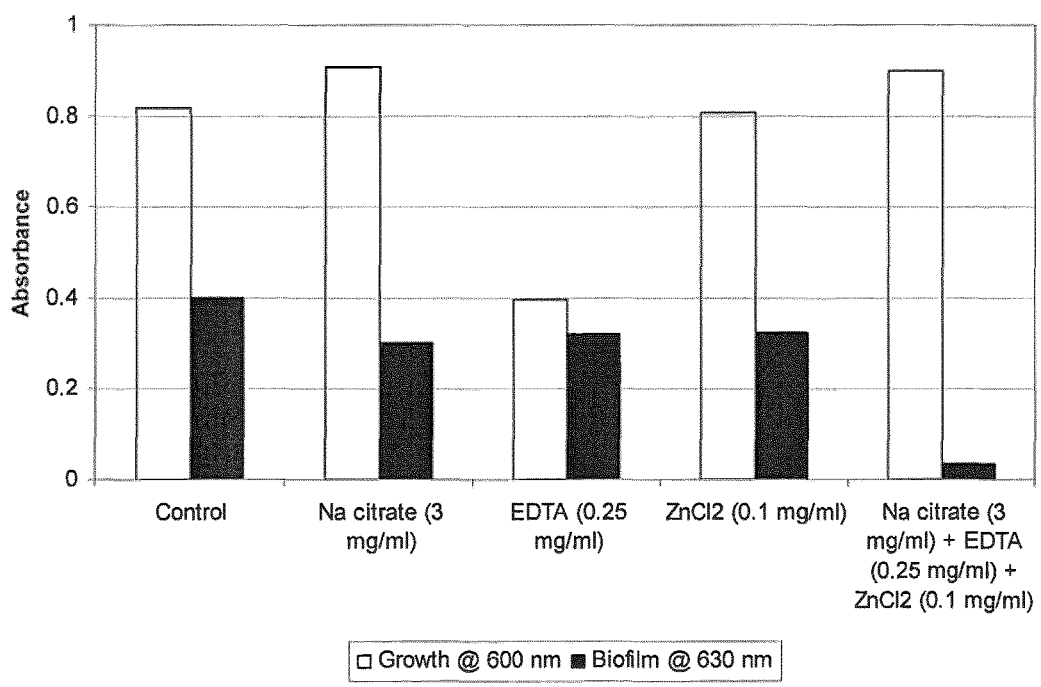
FIG. 10 is a bar graph showing the inhibitory effect of sodium citrate (3 mg/ml), EDTA (0.25 mg/ml) and $ZnCl_2$ (0.1 mg/ml) alone, and in combination on *Escherichia coli* O157:H7 growth and biofilm formation

An overnight broth culture of *E. coli* O157:H7 was grown in TSB and used as inoculum. 96-well microtiter plates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising sodium citrate, EDTA, and $ZnCl_2$ showed an enhanced inhibitory effect on biofilm formation, as compared to sodium citrate, or EDTA, or zinc chloride alone (FIG. 10).

Example 11: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Staphylococcus epidermidis*

Figure 11:
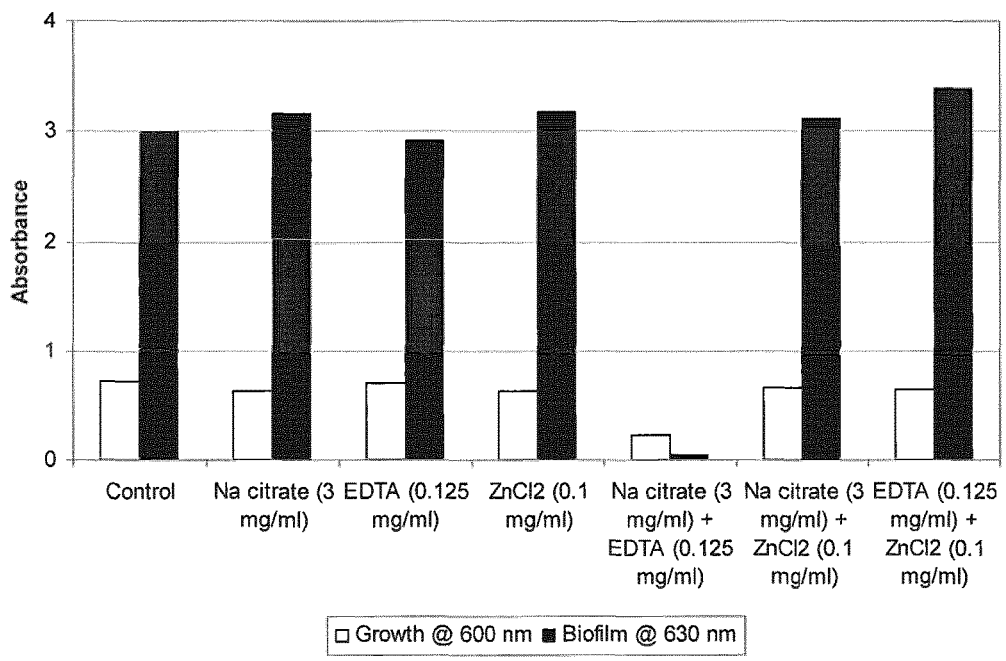
FIG. 11 is a bar graph showing the inhibitory effect of sodium citrate (3 mg/ml), EDTA (0.125 mg/ml) and $ZnCl_2$ (0.1 mg/ml) alone, and sodium citrate+EDTA, sodium citrate+$ZnCl_2$, and EDTA+$ZnCl_2$ combinations on *Staphylococcus epidermidis* growth and biofilm formation

An overnight broth culture of *S. epidermidis* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$ and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 11).

Example 12: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on Coagulase-Negative Staphylococci (CoNS-42)

Figure 12:
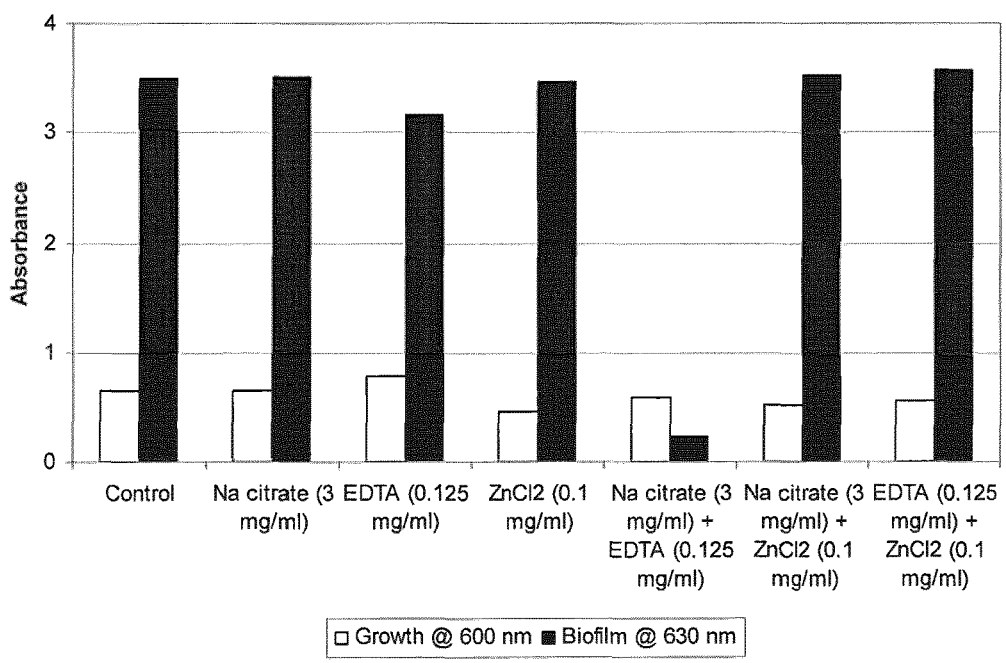
FIG. 12 is a bar graph showing the inhibitory effect of sodium citrate (3 mg/ml), EDTA (0.125 mg/ml) and $ZnCl_2$ (0.1 mg/ml) alone, and sodium citrate+EDTA, sodium citrate+$ZnCl_2$, and EDTA+$ZnCl_2$ combinations on Coagulase-negative Staphylococci (CoNS-42) growth and biofilm formation

An overnight broth culture of CoNS-42 was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 12).

Example 13: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Streptococcus agalactiae* ATCC 12386

Figure 13:
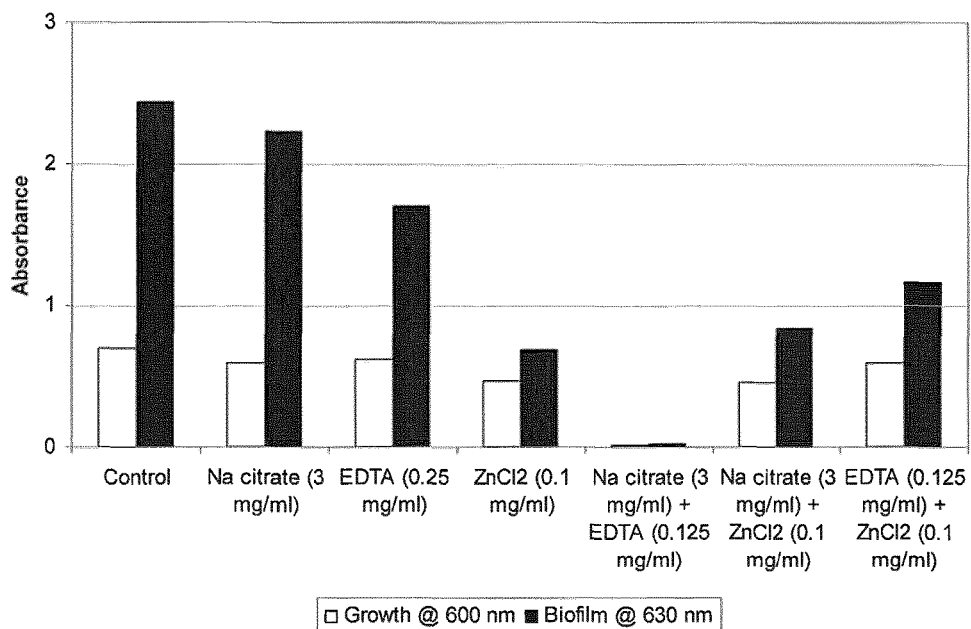
FIG. 13 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Streptococcus agalactiae* ATCC 12386 growth and biofilm formation

An overnight broth culture of *S. agalactiae* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 13).

Example 14: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Klebsiella pneumoniae*

Figure 14:
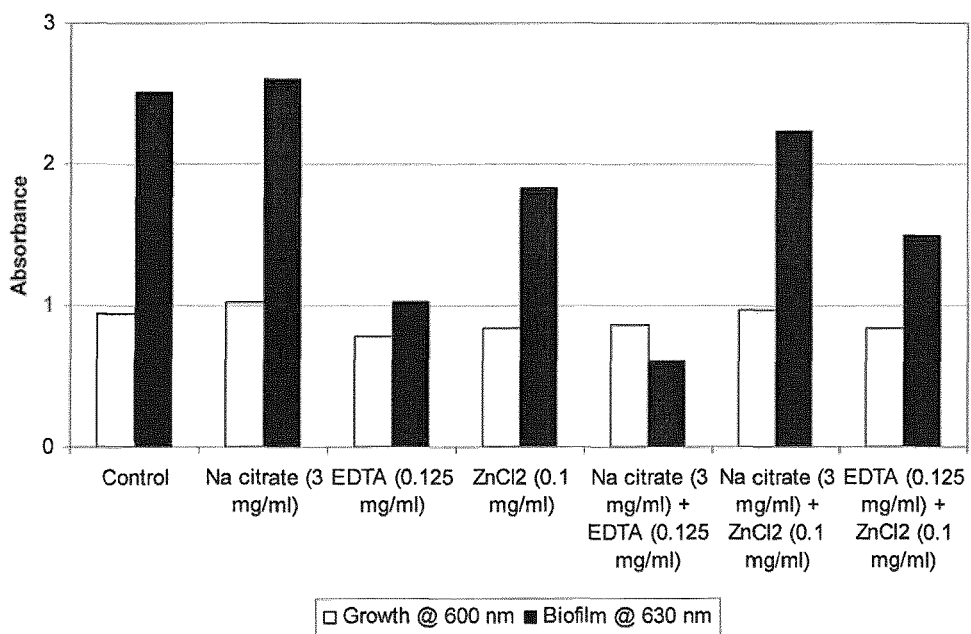
FIG. 14 is a bar graph showing the inhibitory effect of sodium citrate (3 mg/ml), EDTA (0.125 mg/ml) and $ZnCl_2$ (0.1 mg/ml) alone, and sodium citrate+EDTA, sodium citrate+$ZnCl_2$, and EDTA+$ZnCl_2$ combinations on *Klebsiella pneumoniae* growth and biofilm formation

An overnight broth culture of *K. pneumoniae* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 14).

Example 15: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Acinetobacter baumannii*

Figure 15:
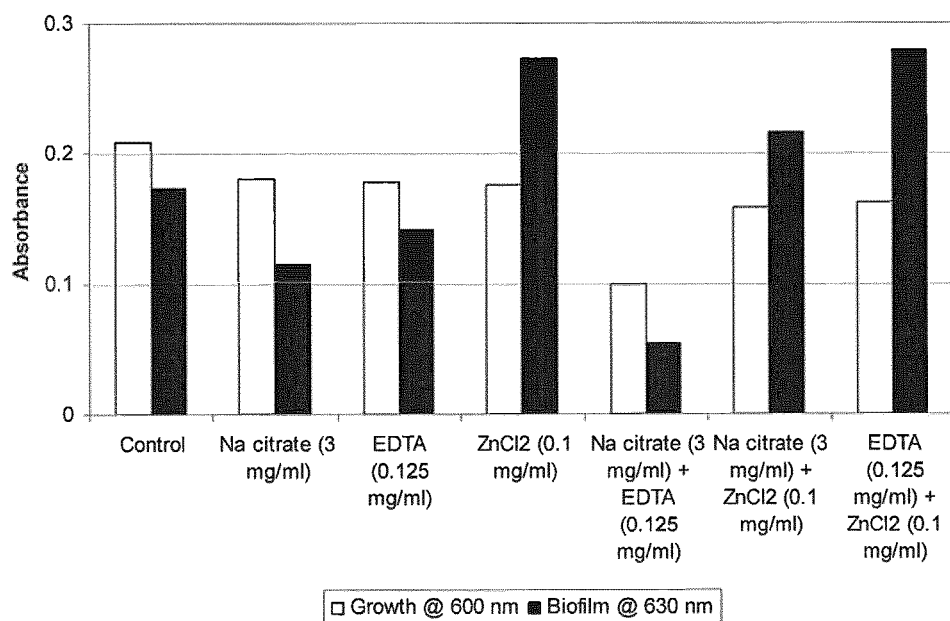
FIG. 15 is a bar graph showing the inhibitory effect of sodium citrate (3 mg/ml), EDTA (0.125 mg/ml) and $ZnCl_2$ (0.1 mg/ml) alone, and sodium citrate+EDTA, sodium citrate+$ZnCl_2$, and EDTA+$ZnCl_2$ combinations on *Acinetobacter baumannii* growth and biofilm formation

An overnight broth culture of *A. baumannii* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 15).

Example 16: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Stenotrophomonas maltophilia*

Figure 16:
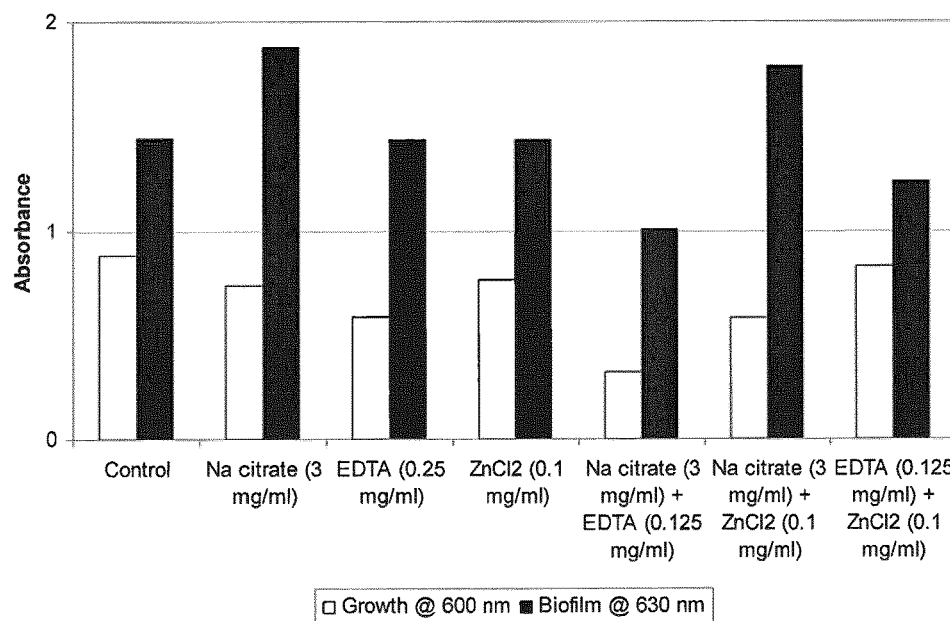
FIG. 16 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Stenotrophomonas maltophilia* growth and biofilm formation

An overnight broth culture of *S. maltophilia* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 16).

Example 17: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on Vancomycin-Resistant *Enterococci* (VRE)

Figure 17:
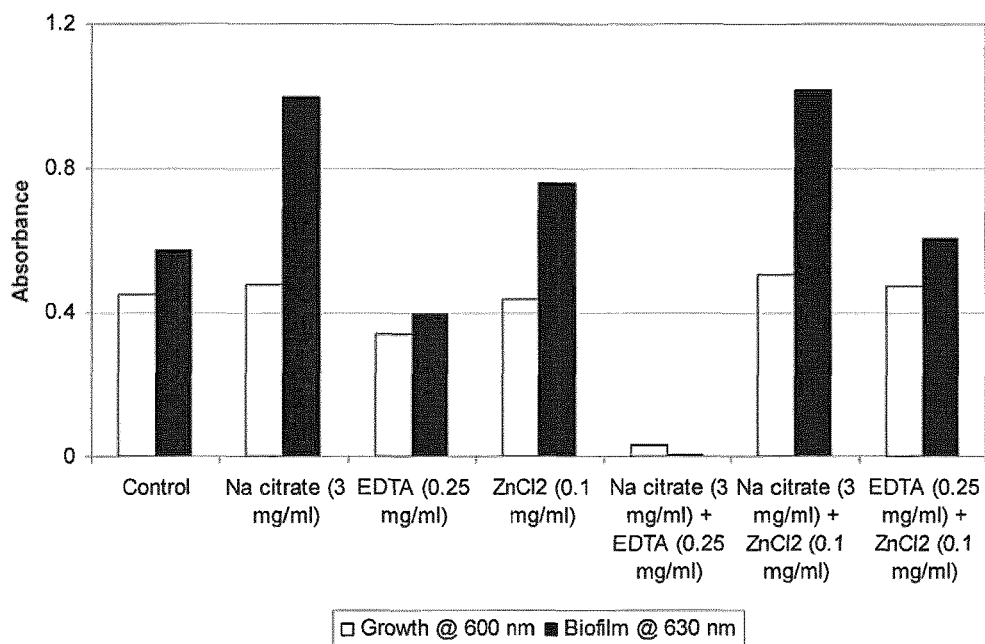
FIG. 17 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on Vancomycin-resistant *Enterococci* (VRE) growth and biofilm formation

An overnight broth culture of VRE was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 17).

Example 18: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Enterococcus faecalis*

Figure 18:
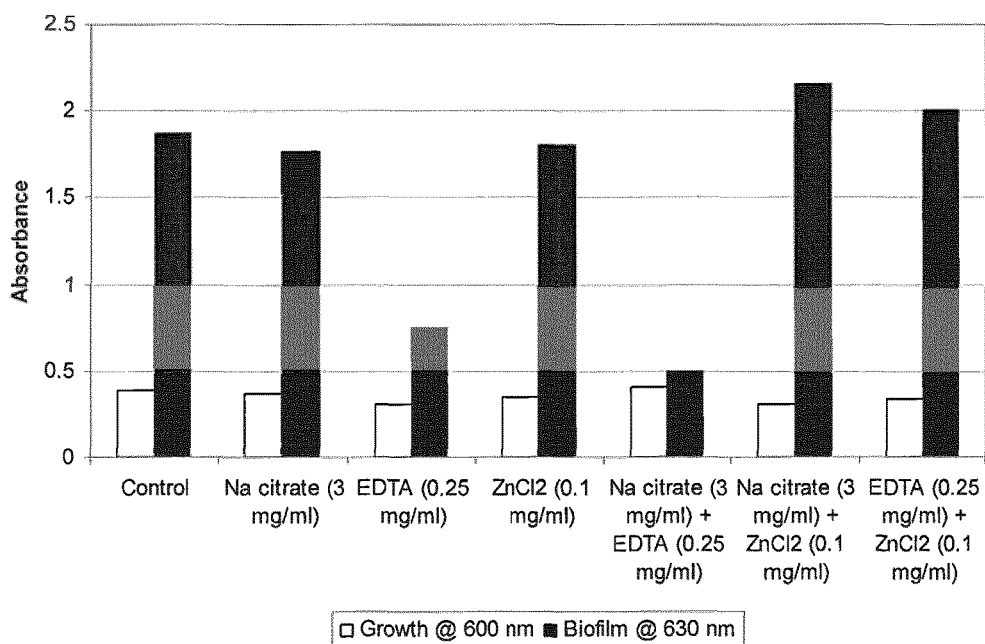
FIG. 18 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Enterococcus faecalis* growth and biofilm formation

An overnight broth culture of *E. faecalis* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 18).

Example 19: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Proteus mirabilis*

Figure 19:
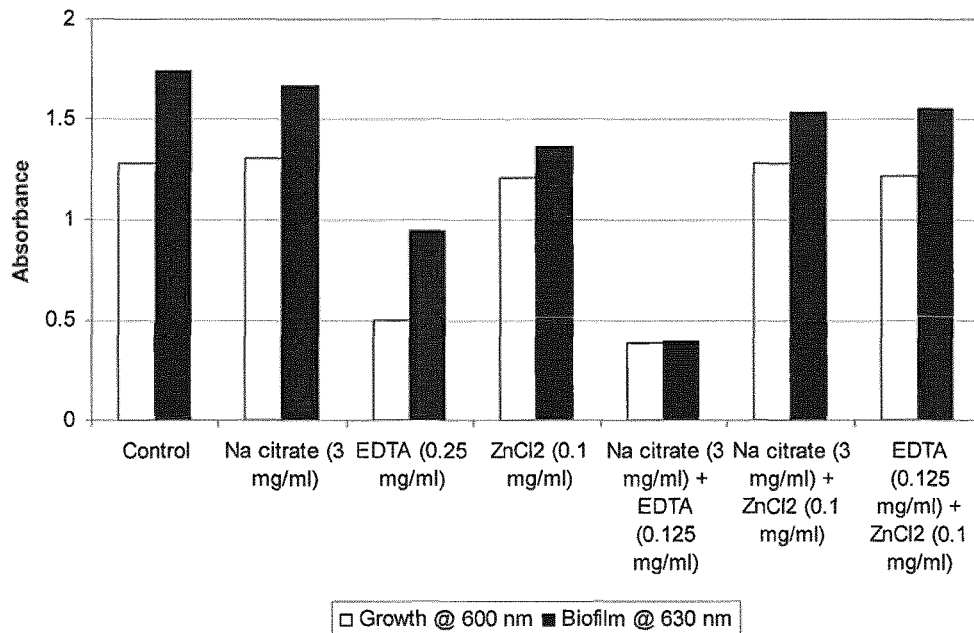
FIG. 19 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Proteus mirabilis* growth and biofilm formation

An overnight broth culture of *P. mirabilis* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 19).

Example 20: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Candida albicans*

Figure 20:
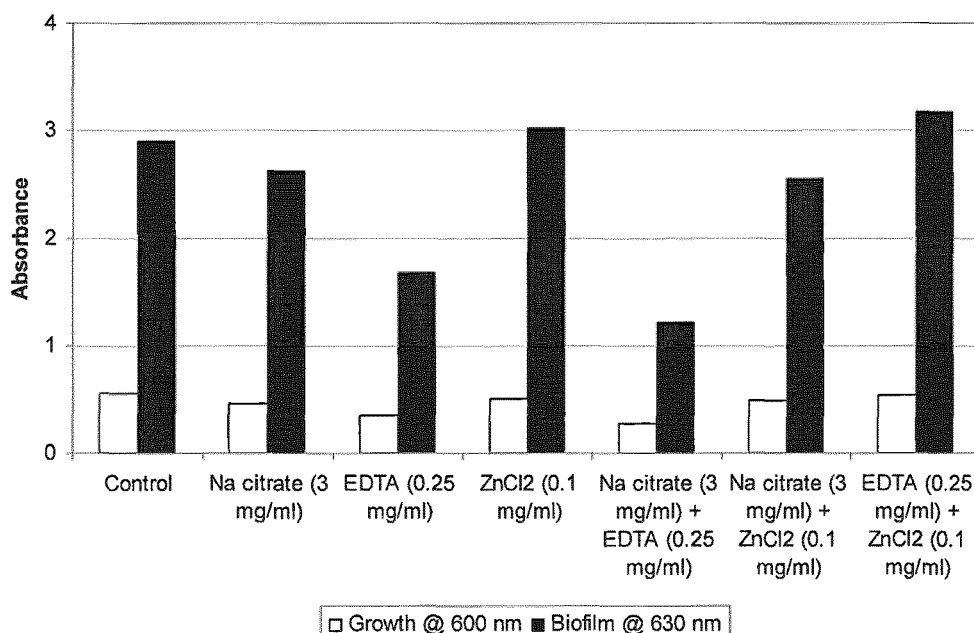
FIG. 20 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Candida albicans* growth and biofilm formation

An overnight broth culture of *C. albicans* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 20).

Example 21: Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Malassezia pachydermatis*

Figure 21:
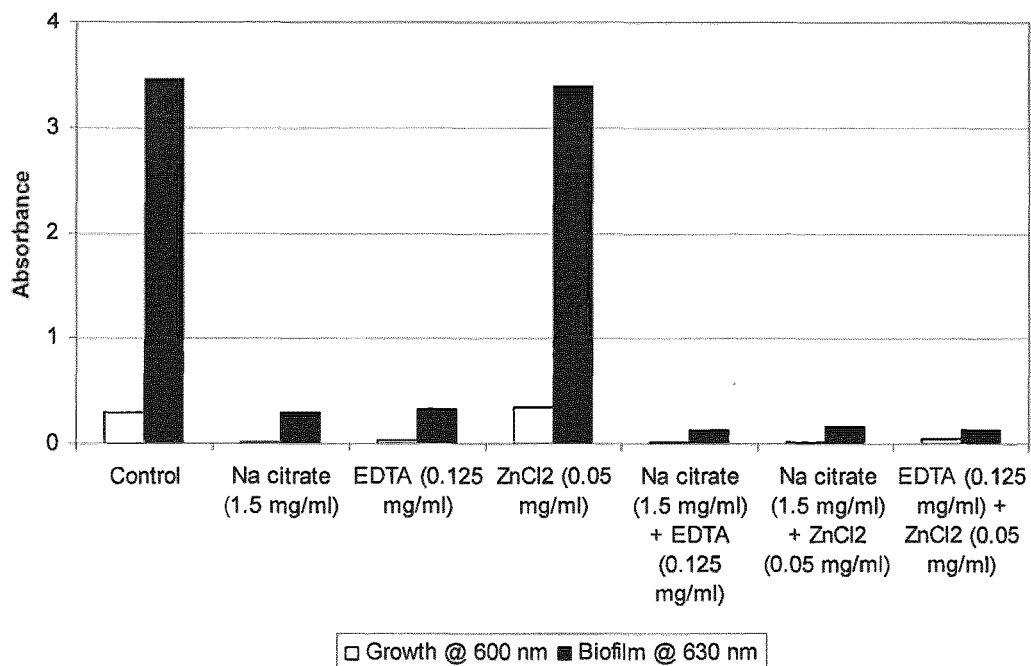
FIG. 21 is a bar graph showing the inhibitory effect of sodium citrate (1.5 mg/ml), EDTA (0.125 mg/ml) and $ZnCl_2$ (0.05 mg/ml) alone, and sodium citrate+EDTA, sodium citrate+$ZnCl_2$, and EDTA+$ZnCl_2$ combinations on *Malassezia pachydermatis* growth and biofilm formation

An overnight broth culture of *Malassezia pachydermatis* was grown in Sabouraud Dextrose Broth and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA, Sodium citrate+ZnCl2, and EDTA+ZnCl2 combinations showed an enhanced inhibitory effect on biofilm formation, as compared to sodium citrate, or EDTA or zinc chloride alone (FIG. 21).

Example 22: Inhibitory Effect of Sodium Citrate, EDTA and $ZnCl_2$ Alone and in Combination on *Malassezia pachydermatis*

Figure 22:
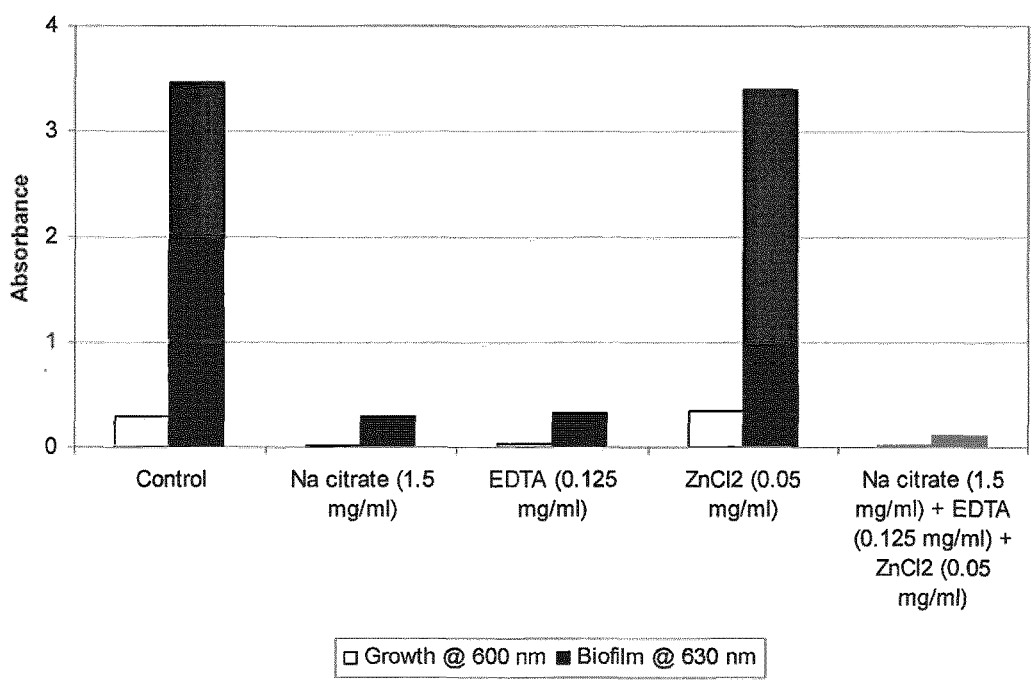
FIG. 22 is a bar graph showing the inhibitory effect of sodium citrate (1.5 mg/ml), EDTA (0.125 mg/ml) and $ZnCl_2$ (0.05 mg/ml) alone and in combination on *Malassezia pachydermatis* growth and biofilm formation

An overnight broth culture of *Malassezia pachydermatis* was grown in Sabouraud Dextrose Broth and used as inoculum. 96-well microtiter plates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising sodium citrate, EDTA, and $ZnCl_2$ showed an enhanced inhibitory effect on biofilm formation, as compared to sodium citrate, or EDTA, or zinc chloride alone (FIG. 22).

We claim:

1. A composition for inhibiting growth of methicillin-resistant *Staphylococcus aureus*, *Staphylococcus epidermidis*, *Streptococcus agalactiae* ATCC 12386, *Acinetobacter baumannii*, *Stenotrophomonas maltophilia*, Vancomycin-resistant *Enterococci*, *Proteus mirabilis*, or biofilm formation in bacteria associated with wound infections comprising:
   (a) disodium or tetrasodium EDTA in a concentration of between about 0.125 mg/mL and about 0.25 mg/mL of the composition
   (b) sodium citrate or potassium citrate in a concentration of between about 1.5 mg/mL and about 3 mg/mL of the composition; and optionally
   (c) a zinc salt selected from the group consisting of zinc chloride, zinc gluconate, zinc lactate, zinc citrate, zinc sulfate, and zinc acetate.

2. The composition of claim 1, comprising disodium EDTA and sodium citrate.

3. The composition of claim 1, wherein the zinc salt is zinc chloride.

4. The composition of claim 2, selected from the group consisting of:
   a. disodium EDTA and sodium citrate, and
   b. sodium citrate, disodium EDTA and zinc chloride.

5. The composition of claim 1, wherein the zinc chloride is between about 500 mg/L and about 5000 mg/L.

6. The composition of claim 1, wherein the zinc chloride is between about 1,000 mg/L-5,000 mg/L.

7. The composition of claim 1, wherein the zinc chloride is between about 500 mg/L-1,000 mg/L.

8. The composition of claim 1, wherein zinc chloride is between about 100 mg/L-500 mg/L.

9. The composition of claim 1, further comprising one or more ingredients selected from the group consisting of: water, a buffer, a stabilizing agent, a gelling agent, a surfactant, a herbal, a vitamin, a mineral, an extra cellular matrix, an antimicrobial, an antibiotic, and a pH adjuster.

10. The composition of claim 1 prepared as one or more of a disinfecting solution, a dip solution, a lotion, a cream, an ointment, a gel, a spray, a dressing, a gauze, a bandage, a thermoreversible gel spray, a wrap, an adhesive, a tape, and a balm.

11. The composition as claimed in claim 1, wherein the composition is delivered using a liposomal or nanoparticle or a suitable device delivery system.

12. The composition as claimed in claim 1, further comprising an anti-infective compound selected from the group consisting of DispersinB, alginate lyase, nisin, lactoferricin, serotransferrin, ovotransferrin, ovalbumin, ovomucoid, protamine sulfate, chlorhexidine, cetylpyridinium chloride, triclosan, silver sulfadiazine, benzalkonium chloride, hydrogen peroxide, citric acid, potassium citrate, 5-fuorouracil, cis-2-decenoic acid, DNase I, proteinase K, silver, gallium, bacteriocins and antimicrobial peptides.

13. A method of preventing or treating wound infection, comprising topical or non-topical use of the composition of claim 1, wherein the wound infection is selected from one or more of infections of cuts, bruises, surgical sites, lacerations, abrasions, punctures, incisions, gunshots, burns, pyoderma, otitis media, otitis externa and/or interna, cow udder mastitis, atopic dermatitis, eczema, pressure ulcers, venous and artery leg ulcers, and diabetic foot ulcers.

14. The method as set forth in claim 13, further comprising multiple applications of the composition.

15. The method as claimed in claim 13, wherein the method is used to treat one or more of humans, domestic animals, farm animals, zoo animals, dogs, horses, cats, cattle, pigs, goats and sheep.

16. A method of preventing or treating meat spoilage comprising topical or non-topical use of the composition of claim 1 on meat or meat products.

17. A method of disinfecting meat comprising topical use of the composition of claim 1 on meat or meat products.

18. The method of claim 16, wherein the meat or meat products comprises intestine or intestinal parts of pigs, cattle, sheep, goats or horses; collagen; collagen or cellulose used for making artificial sausage casings.

19. The method of claim 16, wherein the method comprises one or more of coating, spraying, misting, injecting, soaking, flushing, dipping and rinsing.

20. The composition of claim 1, comprising:
   about 0.125 mg/ml disodium or tetrasodium EDTA and
   about 3 mg/ml sodium citrate or potassium citrate.

21. The composition of claim 1, comprising:
   about 0.25 mg/ml disodium or tetrasodium EDTA and
   about 3 mg/ml sodium citrate or potassium citrate.

22. The composition of claim 1, comprising:
   about 0.125 mg/ml disodium or tetrasodium EDTA and
   about 1.5 mg/ml sodium citrate or potassium citrate.

* * * * *